United States Patent [19]

Wagnon et al.

[11] Patent Number: 4,522,824
[45] Date of Patent: Jun. 11, 1985

[54] INDOLE DERIVATIVES OF TRYPTAMINE AND CARDIOVASCULAR COMPOSITIONS THEREOF

[75] Inventors: Jean Wagnon, Montpellier; Patrick Gautier, Courmonterral; Jean-Pierre Gagnol, St. Martin de Londres, all of France

[73] Assignee: Sanofi, Paris, France

[21] Appl. No.: 477,494

[22] Filed: Mar. 21, 1983

[30] Foreign Application Priority Data

Mar. 23, 1982 [FR] France .................. 82 04921

[51] Int. Cl.³ .................. A61K 31/40; C07D 403/12
[52] U.S. Cl. .................. 514/414; 548/455; 548/507
[58] Field of Search .................. 548/507, 455; 424/274

[56] References Cited

U.S. PATENT DOCUMENTS 4,115,409 9/1978 Large et al. .................. 548/507 X
4,234,595 11/1980 Kreighbaum .................. 548/507 X
4,404,217 9/1983 Demarne et al. .................. 548/507 X Primary Examiner—Glennon H. Hollrah
Assistant Examiner—D. B. Springer
Attorney, Agent, or Firm—Bacon & Thomas

[57] ABSTRACT

The present invention relates to derivatives of tryptamine of formula:

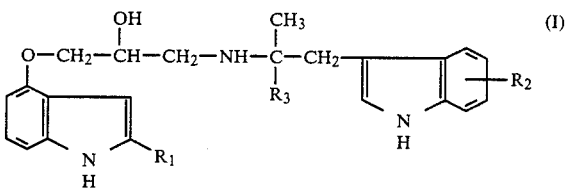

in which:

$R_1$ represents a $CH_2OH$ group, a $-C{\equiv}N$ group, a 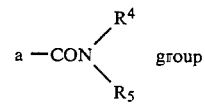 group or a $-COOR_6$ group in which $R_4$, $R_5$ and $R_6$ denote a lower alkyl group or hydrogen;

$R_2$ represents hydrogen or a $C{\equiv}N$ group;

$R_3$ denotes hydrogen, a $CH_3$ group or a $CH_2OH$ group, and the addition salts of the products of formula I with the pharmaceutically acceptable, mineral or organic acids. It also relates to a process for preparing said compounds and to the drugs active on the cardiovascular system, containing said compounds.

7 Claims, No Drawings

INDOLE DERIVATIVES OF TRYPTAMINE AND CARDIOVASCULAR COMPOSITIONS THEREOF

European Patent Applications published under Nos. 14951 and 45911 describe compounds with β-blocking action derived from 4-hydroxy indole. These European Patent Applications correspond respectively to U.S. Pat. Nos. 4,346,093 and 4,404,217.

British Patent Application published under No. 2 001 633 which corresponds to U.S. Pat. Nos. 4,314,943 and 4,234,595; describes derivatives of dimethyltryptamine substituted on the aliphatic nitrogen by a 3-aryloxy 2-hydroxy propyl group.

Finally, European Patent Application No. 25727 describes derivatives of methyltryptamine substituted on the aliphatic nitrogen by an aryloxy or 3-heteroaryloxy 2-hydroxy propyl group.

It is an object of the present invention to provide compounds endowed with β-blocking activity and bereft as far as possible of the sometimes undesirable secondary activities encountered in this type of product when treating hypertension.

The present invention relates as new products to chemical substances derived from tryptamine as well as their acid addition salts. It also relates to a process for preparing these compounds as well as to application thereof in therapeutics.

The compounds according to the invention are selected from the group constituted by:

(a) the compounds responding to general formula:

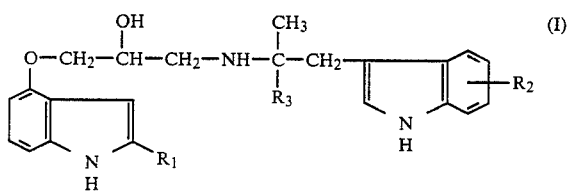

in which:

$R_1$ represents a $CH_2OH$ group, a $-C\equiv N$ group,

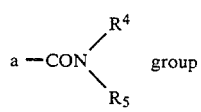

or a $-COOR_6$ group in which $R_4$, $R_5$ and $R_6$ denote a lower alkyl group or hydrogen;

$R_2$ represents hydrogen or a $C\equiv N$ group;

$R_3$ denotes hydrogen, a $CH_3$ group or a $CH_2OH$ group.

(b) The addition salts which compounds (I) are capable of giving with pharmaceutically acceptable, organic or mineral acids, such as hydrochloric acid, citric acid, maleic acid, fumaric acid, tartric acid and acetic acid.

In the present specification, the term lower alkyl group is understood to mean a straight or branched alkyl group comprising from 1 to 4 carbon atoms.

When $R_3$ represents a $CH_3$ group, compounds (I) comprise only one asymmetrical carbon atom at the level of the alcohol function and may exist in the form of two optical isomers R and S. When $R_3$ is H or $CH_2OH$, the carbon bearing $R_3$ is itself an asymmetrical carbon atom and compounds (I) possess two centres of asymmetry. Consequently, there exist four stereoisomers of compounds (I): RR, RS, SR and SS. Both the optical isomers and the stereoisomers form an integral part of the invention.

Compounds (I) may be obtained by the following reaction:

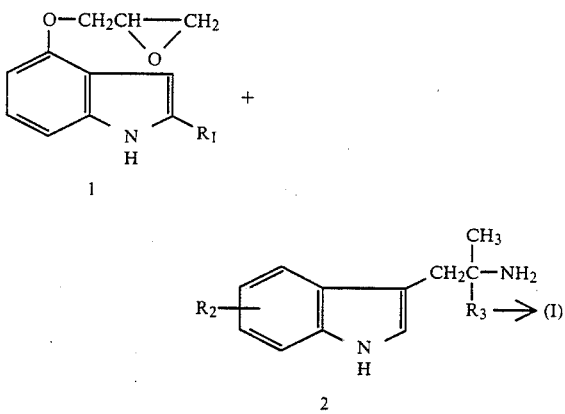

Condensation of the epoxides 1 with the amines 2 may be effected by heating the two substances in equimolecular quantities between 100° and 140° C. When the speed of reaction is too slow, it may be accelerated by the addition of a catalyst such as phenol.

Condensation may also be effected by heating the two reagents in solution in a hydroxyl solvent such as ethanol. Operation is most often carried out at the boiling temperature of the solvent.

As far as the starting products are concerned:

The epoxides 1 are known. They may in particular be obtained by action of epichlorohydrine on the corresponding phenol. In the particular case of $R_1$ representing $-C\equiv N$, the epoxide 1 is obtained in known manner by dehydration of the epoxide where $R_1$ is $-CONH_2$.

The derivatives of tryptamine 2 are known or may be obtained by known processes. In particular when $R_3$ designates H or $CH_3$, compounds 2 may be prepared from the derivatives of gramine according to the method described in Journal of American Chemical Society 69, 3140–3142, (1947).

When $R_3$ denotes $-CH_2OH$, compounds 2 may be obtained by reduction of the corresponding derivatives of the tryptophane according to the method described in Biochimica Biophysica Acta, 341, 284, (1974).

Finally, when $R_2$ denotes $C\equiv N$, compounds 2 may be obtained from the corresponding brominated derivative by action of copper cyanide within a solvent such as N-methyl-pyrrolidone.

The following examples illustrate the invention without limiting the scope thereof.

EXAMPLE 1

4-[3-[2-(3-indolyl)1,1-dimethyl ethylamino]2-hydroxy propoxy]2-ethoxycarbonyl indole. (CM 40 593)

(I) $R_1 = -COOC_2H_5$; $R_2 = H$; $R_3 = -CH_3$ (a) 4-(2,3-epoxy propoxy)2-ethoxycarbonyl indole 4.2 g of 4-hydroxy 2-ethoxycarbonyl indole and 40 ml of epichlorohydrine are dissolved by heating in an inert atmosphere in 40 ml of absolute ethanol then 0.82 g of sodium hydroxide in pellet form is added and the mixture is taken to reflux for 5 hours. Water is added to the reaction mixture and it is neutralized by the addition of acetic acid. The solvents are evaporated in vacuo then extracted with methylene chloride. The organic solution is dried over sodium sulfate and the solvent is evaporated to dryness in vacuo. The residue is chromatographed over a column of silica gel. By elution with the ether-pentane (80–20 vol/vol) mixture, the expected compound is obtained (3.5 g), m.p.: 142°–144° C.

(b) CM 40 593

The mixture of 3.5 g of the compound obtained hereinabove and 3 g of 2-(3-indolyl 1,1-dimethyl ethylamine in 50 ml of ethanol is taken to the reflux for 15 hours. The solvent is evaporated in vacuo then the residue is chromatographed over a column of silica gel.

By eluting with the ethyl acetate-ethanol (90–10 vol/vol) mixture, the expected compound is obtained (2.8 g). After recrystallization in acetonitrile, m.p.: 137°–142° C.

EXAMPLES 2 TO 14

By operating as in Example 1(b) but by varying the reagents used, the different products (I) shown in Table I hereinafter have been isolated.

EXAMPLE 15

4-[3-[(5-cyano 3-indolyl)1,1-dimethyl ethylamino]2-hydroxy propoxy]2-ethoxycarbonyl indole, neutral fumarate (SR 41831A)

(I) $R_1 = $ —COOCH$_2$CH$_3$; $R_2 = $ (5)—CN; $R_3$—CH$_3$ (a) 2-(5-cyano 3-indolyl)1,1-dimethyl ethylamine A mixture of 6.45 g of 2-(5-bromo 3-indolyl)1,1-dimethyl ethylamine and 3.25 g of copper cyanide in 40 ml of N-methylpyrrolidone is heated to reflux for 5 hours.

The solvent is evaporated at 80° C. in vacuo, then the residue is taken up in 50 ml of a 40% ammonia solution; chloroform is added and the mixture is stirred for 30 minutes. The insoluble matter is filtered and washed 5 times with 30 ml of boiling chloroform. The organic phase is separated, washed with water, dried over sodium sulfate and the solvent is evaporated to dryness in vacuo.

Chromatography is effected over a column of silica gel. By eluting with the ethyl acetate-methanol (80–20 vol/vol) mixture, the expected product is obtained. It is recrystallized in ether after decoloration with animal black; weight: 1.4 g; m.p.: 145° C.

(b) SR 4183A

Operation is as in Example 1(b), from the 2-(5-cyano 3-indolyl)1,1-dimethyl ethylamine obtained hereinabove.

By the same treatment, the expected product is obtained in the form of an oily base. This base is converted into neutral fumarate by heating to boiling with a stoichiometric quantity of fumaric acid within absolute ethanol.

After recrystallization in ethyl acetate-ethanol, m.p.: 246°–248° C.

The products of the invention have been studied with a view to determining their pharmacological activity and more especially their activity on the cardiovascular system.

The products of the invention were subjected to the pharmacodynamic tests indicated hereinbelow.

In vivo pharmacological action in the dog

The dog is anaesthetized with sodium pentobarbital, administered by the intravenous route at the dose of 30 mg/kg. A cannula placed in the short saphenous vein allows the products to be injected intravenously. The animal is intubated and allowed to breathe spontaneously.

The cardiac frequency (C.F.) and the systemic arterial pressure (A.P.) and the parameter $(dP/dt)p^{-1}$ max which expresses the cardiac contractility are recorded with the aid of catheters and the variations in these parameters are measured after intravenous injection of the product to be tested, each product being tested at increasing doses.

Antagonism of the effects of isoprenaline

The antagonism of the products with respect to the stimulating cardiovascular effects of isoprenaline on the β-adrenergic receptors was sought. The results are shown in Table II hereinafter and expressed in $ID_{80}$: this is the dose expressed in mg/kg which provokes inhibition of 80% of the tachycardia induced by the isoprenaline administered by the intravenous route.

Antagonism of the effects of noradrenaline

The antagonism of the products with respect to the vascular effects provoked by the intravenous administration of noradrenaline on the α-adrenergic receptors was sought. The results shown in Table II are expressed in $ID_{50}$: this is the dose (mg/kg) which provokes the inhibition of 50% of the pressive response due to the intravenous administration of noradrenaline.

After intravenous administration, the tested compounds therefore present a beta blocking profile whose intensity is greater than that of the propanolo taken as reference product. Their duration of action is long (more than 4 hours).

The same activity is found after administration by the intraduodenal route.

Furthermore, the tested compounds present an alphalytic activity which is weak or zero at the beta-blocking dose.

The compounds according to the invention also show a peripheral vasodilator effect expressed by the reduction in the arterial pressure caused by the reduction of the total peripheral resistances.

This effect is confirmed by the technique of the perfused, isolated paw in the anaesthetized dog by intra-arterial administration of the product to be studied at doses varying from 30 to 1000 μg/ml/minute.

Finally, in the dog subjected to reserpine and anaesthetized, CM 40 593 administered at the dose of 1 mg/kg by the intravenous route shows a slight positive chronotropic effect translating a slight sympathomimetic effect.

The different results on the cardiovascular system obtained in the anaesthetized dog have been confirmed for certain products in the alert dog after administration of the product by the oral route.

It has thus been observed that the compounds of Code Nos. SR 41719A, 41716a, 41779A, 41780A and 41828A, decrease the cardiac frequency or are without action thereon.

This feature, contrary to the characteristic of numerous products of the prior art, is particularly favourable in the treatment of hypertension in man.

In fact, the tachycardia-inducing effect which is frequently observed in the β-blocking products of this family, partially inhibits the antihypertensive effect obtained. In the case of the products according to the invention, the absence of tachycardia-inducing effect allows the antihypertensive effect to manifest itself completely. When there is a bradycardia-inducing effect, this even reinforces the antihypertensive effect of the product.

Finally, the products according to the invention are virtually non-toxic. By way of example, compound CM 40593 presents a median lethal dose ($LD_{50}$) by the oral route of between 3000 and 5000 mg/kg in the male mouse and an $LD_{50}$ of less than 5000 mg/kg in the male rat.

The products according to the invention thus present intrinsic beta-blocking, vasodilator and sympathomimetic properties at the same time.

These products may therefore be used in human therapeutics, particularly for the treatment of hypertension, the treatment of cardiac arrythmias and for the treatment of coronary disease.

The products according to the invention may be presented in the different forms intended for oral administration, such as tablets dosed from 10 to 100 mg, or for rectal administration such as suppositories dosed from 10 to 100 mg, or in the form of injectable preparations containing from 5 to 50 mg of active ingredient.

The usual dosage is from 2 to 4 20 mg tablets per day, but, exceptionally, under medical surveillance, it may exceed these figures.

Some examples of galenic preparation are indicated hereinafter.

| Tablets | |
|---|---|
| CM 40 593 | 20 mg |
| Microcrystalline cellulose | 160 mg |
| Lactose | 172 mg |
| Magnesium stearate | 8 mg |
| | 360 mg |

| Suppositories | |
|---|---|
| CM 40 593 | 40 mg |
| Suppocire C (injectable mixture of natural fatty acid esters) Labrafil 2130 C (Interesterified hydrogenated palm oil) | qsp 3 g |

TABLE 1

| Code No. | $R_1$ | $R_2$ | $R_3$ | Base or salt | Melting point °C. (Solvent) |
|---|---|---|---|---|---|
| M 41105 | —$CONH_2$ | H | $CH_3$ | Base | 193–7 (ethyl acetate) |
| M 41165 | —$CH_2OH$ | H | $CH_3$ | Base | 156–8 (chloroform) |
| SR41719A | —COOCH(CH$_3$)$_2$ | H | $CH_3$ | Hydrochloride | 144–8 (ethyl acetate-isopropyl ether) (with 1 molecule of water) |
| SR41828A | COOH | H | $CH_3$ | Hydrochloride | 244–6 (aqueous ethanol) |
| SR41370A | —C≡N | H | $CH_3$ | Neutral fumarate | 159–164 (ethyl acetate-ethanol) |
| SR41829A | —CON(CH$_3$)$_2$ | H | $CH_3$ | Neutral fumarate | 223–6 (ethyl acetate-ethanol) |
| SR41830A | —CON((CH$_2$)$_3$CH$_3$)$_2$ | H | $CH_3$ | Neutral fumarate | 147–9 (ethyl acetate-ethanol) |
| SR41716A | $COOCH_2CH_3$ | $CH_3$(5) | $CH_3$ | Neutral fumarate | 252–256 (ethyl acetate-ethanol) |
| SR41779A | $COOCH_2CH_3$ | F(5) | $CH_3$ | Neutral fumarate | 236–239 (ethyl acetate-ethanol) |
| SR41780A | $COOCH_2CH_3$ | Cl(5) | $CH_3$ | Neutral fumarate | 249–251 (ethyl acetate-ethanol) |
| SR41648 | $COOCH_2CH_3$ | $CCH_3$(5) | $CH_3$ | Base | 122–124 (chloroform-isopropyl ether) |
| SR41832 | $COOCH_2CH_3$ | H | $CH_2OH$ | Base | 120–122° C. (ethyl acetate) Isomer non-determined |
| R41294A | $COOCH_2CH_3$ | H | H | Neutral fumarate | 219–221 (ethanol) Mixture of isomers |

TABLE II

| Code No. | β-effect $ID_{80}$ (mg/kg) Iso-prenaline | α-effect $LD_{50}$ (mg/kg) Nora-drenaline | Effects on parameters | | |
|---|---|---|---|---|---|
| | | | CF | AP | $\frac{dP}{dt} p^{-1}$ max |
| CM40593 | 0.1 | 0.1 | = or ↓ | ↓ | ↑ |
| CM41105 | 0.1 | — | weak | ↓ | ↑ |
| CM41165 | 0.05 | — | | ↓ | ↓ |
| SR41828A | 0.3 | — | = or ↓ | ↓ | = |
| SR41370A | 0.05 | 0 | weak | ↓ | ↑ |
| SR41830A | 1 | 0 | | ↓ | ↑ |
| SR41648 | 0.1 | 0 | | ↓ | ↓ |
| SR41832 | 0.1 | 0 | | ↓ | ↓ |
| SR41294A | 0.1 | 0 | | ↓ | ↓ |
| SR41831A | 0.1 | — | | ↓ | ↓ |

What is claimed is:

1. Compounds derived from tryptamine of formula:

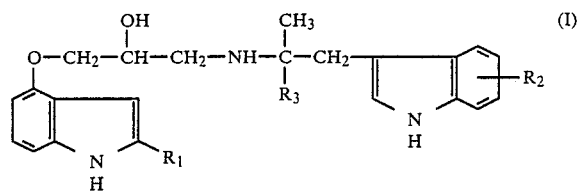

in which:

$R_1$ represents a $CH_2OH$ group, a $-C\equiv N$ group,

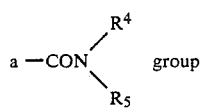

or a $-COOR_6$ group in which $R_4$, $R_5$ and $R_6$ denote a lower alkyl group or hydrogen;

$R_2$ represents hydrogen or a $C\equiv N$ group;

$R_3$ denotes hydrogen, a $CH_3$ group or a $CH_2OH$ group, and the addition salts of the products of formula I with pharmaceutically acceptable, mineral or organic acids.

2. Compounds of claim 1, where $R_1$ is hydrogen, $R_3$ is $CH_3$ and $R_1$ is selected from the group consisting of $-CONH_2$, $-CH_2OH$,

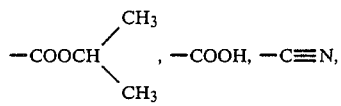

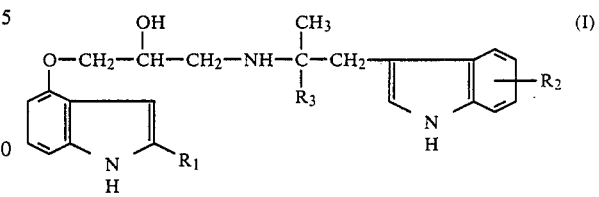

3. The compound of claim 1, wherein $R_1$ is $CHOOCH_2CH_3$, $R_2$ is H and $R_3$ is $CH_2OH$.

4. The compound of claim 1, wherein $R_1$ is $COOCH_2CH_3$; and $R_2$ and $R_3$ are hydrogen.

5. Compounds derived from tryptamine having a formula:

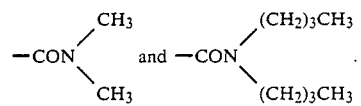

in which:

$R_1$ is $-COOCH_2CH_3$, $R_3$ is $-CH_3$ and $R_2$ is selected form the group consisting of $-CH_3$, $-F$, $-Cl$, and $-OCH_3$.

6. A pharmaceutical composition for the treatment of hypertension, cardiac arrythmias and coronary diseases comprising an effective amount of at least one compound from claim 1 in a pharmaceutically acceptable carrier.

7. An injectable pharmaceutical composition according to claim 6 wherein the effective amount of the compound is from 5 to 50 mg.

* * * * *